United States Patent
Peterson (10) Patent No.: US 10,441,156 B2
(45) Date of Patent: Oct. 15, 2019

(54) APPLICATION OF HIGHLY SCATTERING MATERIALS TO SURGICAL ILLUMINATION

(71) Applicant: Medical Instrument Development Laboratories, Inc., San Leandro, CA (US)

(72) Inventor: Erik William Peterson, Walnut Creek, CA (US)

(73) Assignee: Medical Instrument Development Laboratories, Inc., San Leandro, CA (US)

(*) Notice: Subject to any disclaimer, the term of this patent is extended or adjusted under 35 U.S.C. 154(b) by 534 days.

(21) Appl. No.: 14/849,519

(22) Filed: Sep. 9, 2015

(65) Prior Publication Data
US 2016/0066777 A1   Mar. 10, 2016

Related U.S. Application Data (60) Provisional application No. 62/048,432, filed on Sep. 10, 2014.

(51) Int. Cl.
*A61B 3/00*     (2006.01)
*A61F 9/007*    (2006.01)
*A61B 90/30*    (2016.01)

(52) U.S. Cl.
CPC .......... *A61B 3/0008* (2013.01); *A61F 9/007* (2013.01); *A61B 2090/306* (2016.02)

(58) Field of Classification Search
CPC .......... A61F 9/007; A61F 9/008–009; G02B 6/0001; G02B 6/0005; G02B 6/0006; G02B 6/0008; G02B 6/0013–0065; G02B 6/001; A61B 3/0008; A61B 2090/304; A61B 2090/306; A61B 2090/308; A61B 2090/309; A61B 90/30; A61B 90/35; A61B 1/06–07
See application file for complete search history.

(56) References Cited

U.S. PATENT DOCUMENTS 5,269,777 A * 12/1993 Doiron ............... A61N 5/062
                                                                606/7
5,536,265 A *  7/1996 van den Bergh ...... A61B 18/22
                                                                606/2

(Continued)

FOREIGN PATENT DOCUMENTS

WO        03/065880 A2    8/2003

OTHER PUBLICATIONS

International Search Report from the International Searching Authority for Application No. PCT/US2015/049254 dated Dec. 4, 2015 (9 pages).

(Continued)

*Primary Examiner* — Ellen C Hammond
*Assistant Examiner* — Tessa M Matthews
(74) *Attorney, Agent, or Firm* — Michael Best & Friedrich LLP (57) ABSTRACT

A surgical instrument includes an optical fiber having a proximal end and a distal end, the optical fiber configured to emit light at the distal end. The surgical instrument also includes at least one scattering material coupled to the proximal end, the distal end, or a combination of both the proximal end and the distal end.

15 Claims, 6 Drawing Sheets

(56) References Cited

U.S. PATENT DOCUMENTS

| | | | |
|---|---|---|---|
| 5,908,415 A * | 6/1999 | Sinofsky | A61L 2/10 |
| | | | 606/7 |
| 2002/0028041 A1* | 3/2002 | Easley | G02B 6/0008 |
| | | | 385/31 |
| 2005/0075628 A1 | 4/2005 | Cazzini et al. | |
| 2005/0078910 A1 | 4/2005 | Hickingbotham | |
| 2007/0100327 A1* | 5/2007 | Smith | A61F 9/007 |
| | | | 606/4 |
| 2009/0040598 A1* | 2/2009 | Ito | A61B 1/0638 |
| | | | 359/332 |
| 2009/0122320 A1 | 5/2009 | Petersen et al. | |
| 2011/0082452 A1* | 4/2011 | Melsky | A61B 18/24 |
| | | | 606/15 |
| 2011/0238139 A1* | 9/2011 | Gowda | A61N 5/062 |
| | | | 607/88 |
| 2011/0299295 A1* | 12/2011 | Mochizuki | G02B 6/001 |
| | | | 362/558 |
| 2013/0077917 A1* | 3/2013 | Lassalas | G02B 6/42 |
| | | | 385/37 |
| 2013/0317294 A1 | 11/2013 | Brennan et al. | |
| 2014/0249407 A1 | 9/2014 | Adler et al. | |
| 2014/0316206 A1* | 10/2014 | Vasan | A61B 1/267 |
| | | | 600/191 |

OTHER PUBLICATIONS

Written Opinion from the International Searching Authority for Application No. PCT/US2015/049254 dated Dec. 4, 2015 (4 pages).
Extended European Search Report and Search Opinion for Application No. 15840119.0 dated Mar. 14, 2018 (8 pages.).

* cited by examiner

APPLICATION OF HIGHLY SCATTERING MATERIALS TO SURGICAL ILLUMINATION

CROSS-REFERENCE TO RELATED APPLICATIONS

This application claims priority to U.S. Provisional Application No. 62/048,432, filed Sep. 10, 2014, the entire contents of which are incorporated herein by reference.

BACKGROUND

Surgical lighting systems are often used to enhance viewing of a surgical site, cavity, or other area in a patent by providing lighting to the area of interest. However, current lighting systems do not always provide a desired amount, angle, or breadth of light at the area of interest.

In ophthalmic surgery, for example, a fiberoptic instrument is often used to deliver illumination into the interior of an eye. Similarly, fiberoptics are often used to deliver illumination through endoscopic surgical instruments. However, the cone of light emitted from the end of the optical fiber has a maximum angle (typically 30° or less) limited by the numerical aperture of the fiber.

SUMMARY

In accordance with one construction, a surgical instrument includes an optical fiber having a proximal end and a distal end, the optical fiber configured to emit light at the distal end. The surgical instrument also includes at least one scattering material coupled to the proximal end, the distal end, or a combination of both the proximal end and the distal end.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Surgical instruments for use in ophthalmic surgery are described and illustrated herein. The surgical instruments provide illumination within an eye. While the surgical instruments are described in the context of ophthalmic surgery, embodiments of the invention may also be applied to other surgical applications, including applications in endoscopic surgery.

Figure 1A:
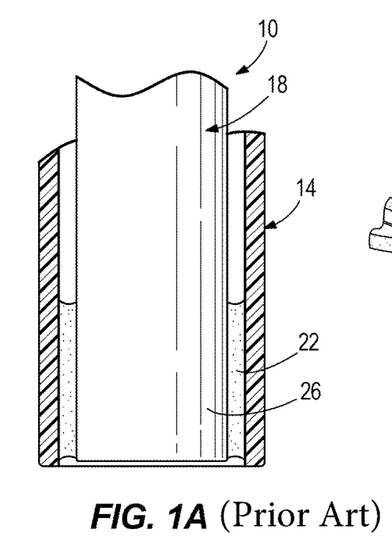
FIG. 1A illustrates a prior-art surgical instrument.
Figure 1B:
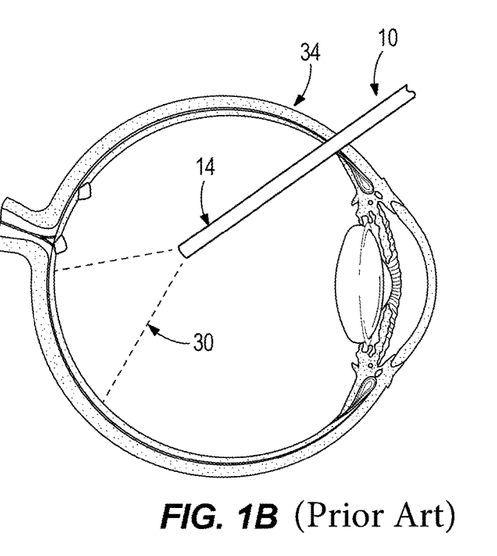
FIG. 1B illustrates the surgical instrument of FIG. 1A inserted into an eye, and further illustrates a beam of light generated by the surgical instrument.

FIGS. 1A and 1B illustrate a surgical instrument 10 found in the prior art. The surgical instrument 10 includes a tube 14 (e.g., hollow tube), a light source in the form of an optical fiber 18 extending through the tube 14, and adhesive 22 between the tube 14 and a distal end 26 of the optical fiber 18. It should be understood, that an optical fiber is more accurately described as a light carrier, but the term light source is often used in the field of ophthalmic surgical instruments. As illustrated in FIG. 1B, a beam of light 30 is directed directly into the interior of an eye 34 from the distal end 26 of the optical fiber 18. The beam of light 30 is relatively narrow, being limited by a numerical aperture of the optical fiber 18.

Figure 2A:
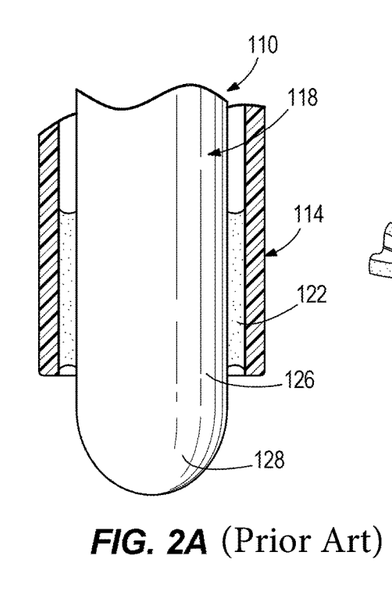
FIG. 2A illustrates another prior-art surgical instrument with a U-shaped (in cross-section) tip.
Figure 2B:
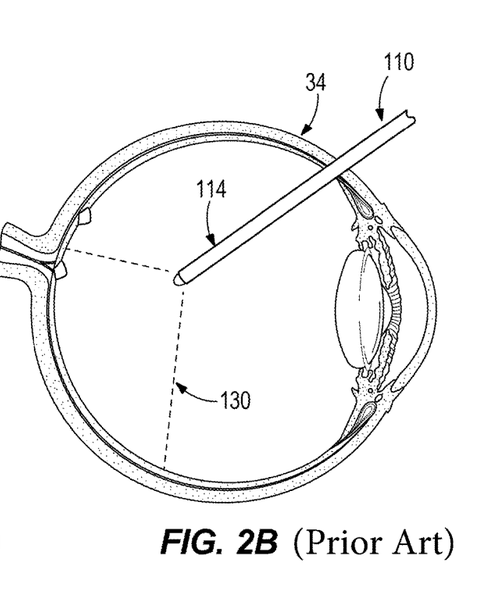
FIG. 2B illustrates the surgical instrument of FIG. 2A inserted into an eye, and further illustrates a beam of light generated by the surgical instrument.

FIGS. 2A and 2B illustrate another surgical instrument 110 found in the prior art. The surgical instrument 110 includes a tube 114 (e.g., hollow tube), a light source in the form of an optical fiber 118 extending through the tube 114, and adhesive 122 between the tube 114 and a distal end 126 of the optical fiber 118. As illustrated in FIG. 2A, a portion 128 of the distal end 126 extends out of the tube 114 and is shaped into a bullet-like tip, with the object of redirecting a beam of light 130 into a wider angle in the eye 34 (FIG. 2B) as compared with the surgical instrument 10 in FIGS. 1A and 1B.

Figures 3A, 3B:
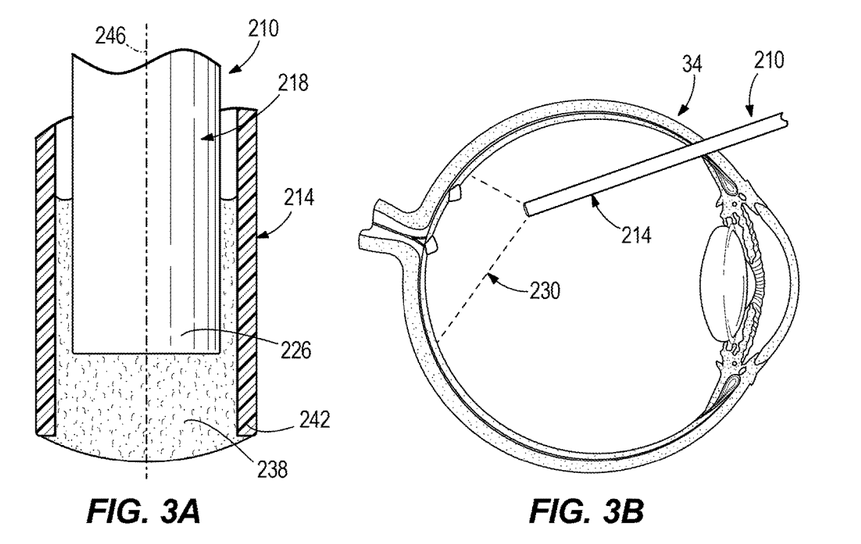
FIG. 3A illustrates a surgical instrument in accordance with one construction, having scattering material disposed within a tube at a distal end of an optical fiber.
FIG. 3B illustrates the surgical instrument of FIG. 3A inserted into an eye, and further illustrates a beam of light generated by the surgical instrument.

In contrast to the figures discussed above, FIGS. 3A and 3B illustrate a surgical instrument 210 according to one construction of the invention. The surgical instrument 210 includes a tube 214 (e.g., hollow tube) and a light source in the form of an optical fiber 218 extending through the tube 214. The optical fiber 218 has a distal end 226. As illustrated in FIG. 3B, a beam of light 230 is emitted from the distal end 226 into the eye 34. The beam of light 230 first passes, however, through a scattering material 238. The scattering material 238 is disposed at least partially within the tube 214, between the distal end 226 of the optical fiber 218 and a distal end 242 of the tube 214. In the illustrated construction, the scattering material 238 is in direct contact with the distal end 226 of the optical fiber 218.

The scattering material 238 is an optical material with a high scattering coefficient and a low absorption coefficient, and is used to enhance delivery of illumination to a surgical operating site (e.g., the inside of the eye 34). Scattering occurs at interfaces between materials with different indices of refraction. One way to form the scattering material 238 is to embed small crystals or particles of one material in a matrix of a second material with a different index of refraction. If both materials have low absorption, desired characteristics are obtained.

In some constructions, the scattering material 238 includes micron-sized crystals of titanium dioxide, which have an extremely high index of refraction, dispersed in an optical-grade epoxy. Such a scattering material 238 can be cast into a variety of useful shapes while the epoxy cures. In some constructions, the scattering material 238 also or alternatively includes micron (or smaller) spheres of silicon dioxide, which have a less extreme index of refraction as compared to the titanium dioxide. In some constructions, the scattering material 238 is integrally formed in one piece with the distal end 226 of the optical fiber 218. For example, in some constructions the distal end 226 of the optical fiber 218 is heated, to melt some of the material (e.g., plastic) of the distal end 226. The distal end 226 is then pressed and twisted into a mold containing titanium and/or silicon dioxide powder. The powder is then embedded into the molten material and the distal end 226 of the optical fiber 218 is shaped as desired.

With continued reference to FIGS. 3A and 3B, as the beam of light 230 emerges from the distal end 226 of the optical fiber 218 and the distal end 242 of the tube 214, the beam of light 230 is scattered by the scattering material 238 into a wide angle, providing wide-angle illumination centered along a longitudinal axis 246 of the tube 214 and the optical fiber 218 (FIG. 3A). The scattering material 238 therefore increases the angle at which light is emitted from the distal end 242 of the tube 214 when compared to a surgical instrument that does not include scattering material (such as in FIGS. 1 and 2).

Figure 4A:
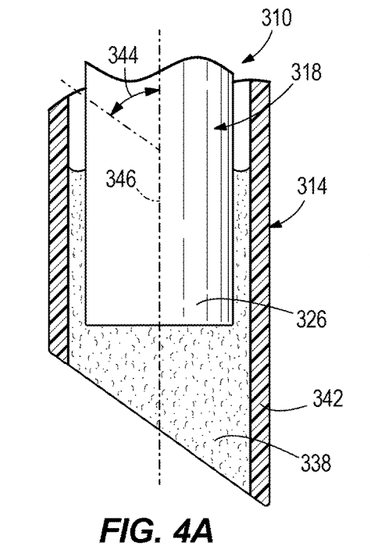
FIG. 4A illustrates a surgical instrument in accordance with another construction, having a tube with an angled end, and scattering material disposed within the tube at a distal end of an optical fiber.
Figure 4B:
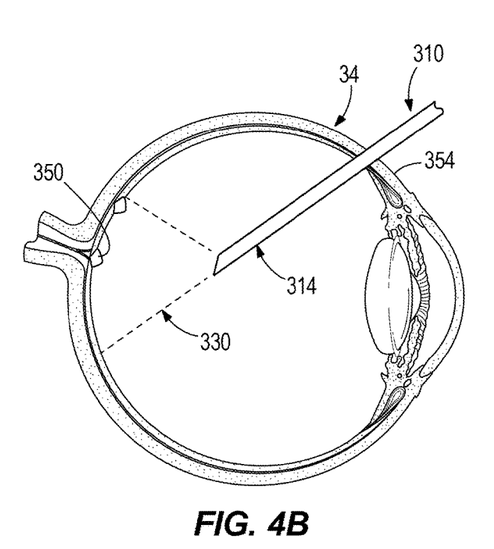
FIG. 4B illustrates the surgical instrument of FIG. 4A inserted into an eye, and further illustrates a beam of light generated by the surgical instrument.

FIGS. 4A and 4B illustrate a surgical instrument 310 according to another construction of the invention. The surgical instrument 310 includes a tube 314 (e.g., hollow tube) and a light source in the form of an optical fiber 318 extending through the tube 314. The optical fiber 318 has a distal end 326. As illustrated in FIG. 4B, a beam of light 330 is emitted from the distal end 326 of the optical fiber 318 into the eye 34. The beam of light 330 first passes through scattering material 338 (e.g., the same type of scattering material as scattering material 238). Similar to the surgical instrument 210, the scattering material 338 is disposed at least partially within the tube 314, between the distal end 326 of the optical fiber 318 and a distal end 342 of the tube 314, and is in direct contact with the distal end 326 of the optical fiber 318. In some constructions, the scattering material 338 is integrally formed in one piece with the distal end 326 of the optical fiber 318, via a method similar to that described above for the scattering material 238. However, as illustrated in FIG. 4A, the distal end 342 of the tube 314 (and of the scattering material 338) is cut at an oblique angle 344 to a longitudinal axis 346 of the tube 314 and the optical fiber 318. As illustrated in FIG. 4B, this oblique angle 344 allows more of the scattered beam of light 330 to be directed to one side of the longitudinal axis 346. This configuration also allows the beam of light 330 to be directed to a posterior pole 350 of the eye 34 without requiring as much angulation of the surgical instrument 310 relative to a wall 354 of the eye 34 in comparison to a surgical instrument without an angled end (e.g., like the surgical instrument 210 in FIGS. 3A and 3B).

Figures 5A, 5B:
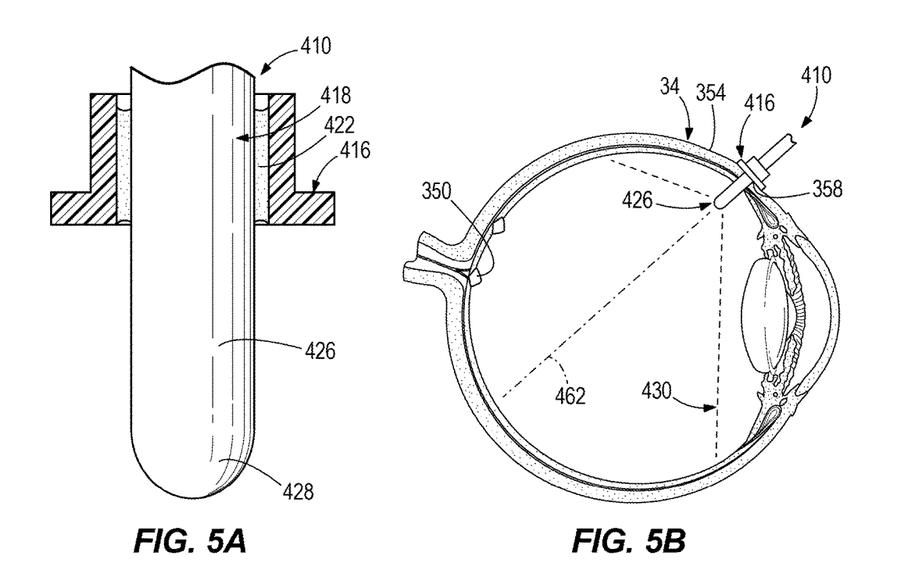
FIG. 5A illustrates another prior art surgical instrument.
FIG. 5B illustrates the surgical instrument of FIG. 5A inserted into an eye, and further illustrates a beam of light generated by the surgical instrument.

FIGS. 5A and 5B illustrate another surgical instrument 410 found in the prior art. The surgical instrument 410 includes a tube in the form of a hub 416, a light source in the form of an optical fiber 418 extending through the hub 416, and adhesive 422 between the hub 416 and a distal end 426 of the optical fiber 418. As illustrated in FIG. 5A, a portion 428 of the distal end 426 of the optical fiber 418 extends out of the hub 416 and is shaped into a bullet-like tip. As illustrated in FIG. 5B, the optical fiber 418 passes through an incision 458 in the wall 354 of the eye 34, with the hub 416 resting on the wall 354. In some constructions another tube (e.g., a cannula) is placed into the incision 458 first, with the optical fiber 418 then being coupled to the cannula. As illustrated in FIG. 5B, a beam of light 430 is emitted from the distal end 426 of the optical fiber 418. The beam of light 430 is wide enough to cover the posterior pole 350 of the eye 34, even though a center 462 of the beam of light 430 is somewhat to the side of the posterior pole 350.

Figures 6A, 6B:
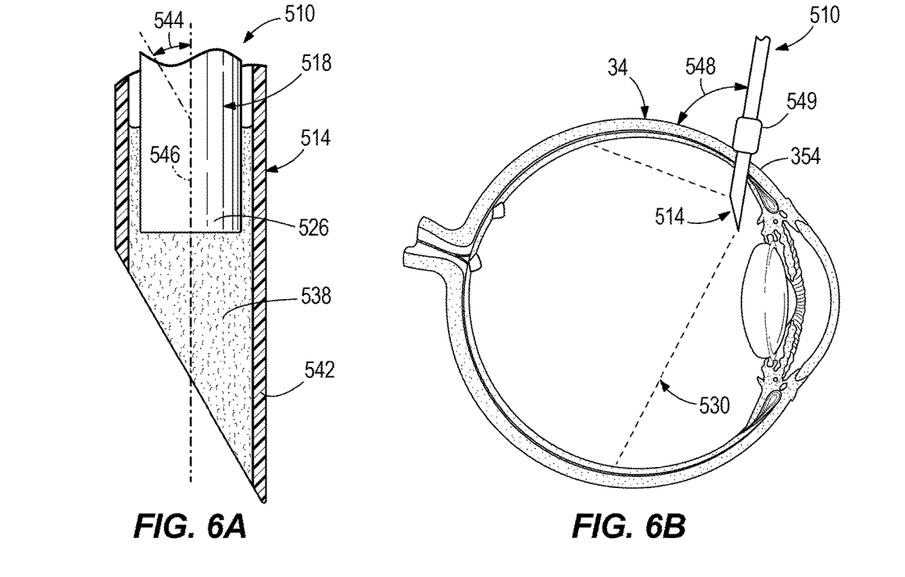
FIG. 6A illustrates a surgical instrument in accordance with another construction, having a tube passing through a hub, the tube having an angled end, and scattering material disposed within the tube at a distal end of an optical fiber.
FIG. 6B illustrates the surgical instrument of FIG. 6A inserted into an eye, and further illustrates a beam of light generated by the surgical instrument.

FIGS. 6A and 6B illustrate a surgical instrument 510 according to another construction of the invention. The surgical instrument 510 includes a tube in the form of a needle 514 (e.g., a hypodermic needle) and a light source in the form of an optical fiber 518 extending through the needle 514. The optical fiber 518 has a distal end 526. As illustrated in FIG. 6B, a beam of light 530 is emitted from the distal end 526 of the optical fiber 518 into the eye 34. The beam of light 530 first passes through a scattering material 538 (e.g., the same type of scattering material as scattering material 238 or 338). The scattering material 538 is disposed at least partially within the needle 514, between the distal end 526 of the optical fiber 518 and a distal end 542 of the needle 514. In some constructions, the scattering material 538 is integrally formed in one piece with the distal end 526 of the optical fiber 518, via a method similar to that described above for the scattering material 238. The distal end 542 of the needle 514 and the scattering material 538 are cut at an oblique angle 544 relative to a longitudinal axis 546 of the needle 514 and the optical fiber 518. The oblique angle 544 is smaller than the oblique angle 344 illustrated in FIG. 4A, such that the distal end 542 of the needle 514 has a sharper profile. In some constructions, the oblique angle 544 is less than 30 degrees. Other constructions include different values and ranges for the oblique angle 344.

The needle 514 is fabricated from a material such as surgical stainless steel, and the oblique angle 544 is sharp enough such that the needle 514 is able to cut through the wall 354 of the eye 34. Thus, the needle 514 can be inserted directly into the eye 34 (FIG. 6B), without the need for a separate incision. The oblique angle 544 also allows the scattered beam of light 530 to be directed at right angles (or nearly at right angles) to the longitudinal axis 546 of the tube 514 and the optical fiber 518. This allows the needle 514 to be inserted at an acute angle 548 relative to the wall 354 of the eye 34, as opposed to being inserted at a perpendicular angle relative to the wall 354.

One advantage of this angled insertion into the eye 34 is that, together with a very small size of the needle 514, a wound left in the wall 354 of the eye 34 after removal of the instrument will tend to seal itself, preventing leakage of intraocular fluids or introduction of pathogens through the wound. A second advantage is that the optical fiber 518 outside of the eye 34 is not perpendicular to the eye 34, as in the surgical instrument 410 shown in FIG. 5A. This makes it easier to route the optical fiber 518 and secure the optical fiber 518 without putting a large strain onto the optical fiber 518 or the optical fiber's insertion through the wall 354 of the eye 34. As illustrated in FIG. 6B, in some constructions the surgical instrument 510 further includes a hub 549 that receives the needle 514 and rests on the wall 354 of the eye 34.

FIGS. 1-4 described above illustrate various surgical instruments that may be held in a surgeon's hand, so that a beam of light may be directed to different parts of the eye 34, while FIGS. 5 and 6 described above illustrate chandelier-type surgical instruments, which may generally be fixed into the wall 354 of the eye 34 and are generally not held by the surgeon's hand. It is common, however, for both types to be used at the same time, such that a chandelier instrument (e.g., the surgical instrument 510 in FIGS. 6A and 6B) provides illumination over a wide area and a hand-held instrument (e.g., the surgical instrument 210 or 310 in FIGS. 3 and 4) directs more intense illumination to a specific area.

Figure 7:
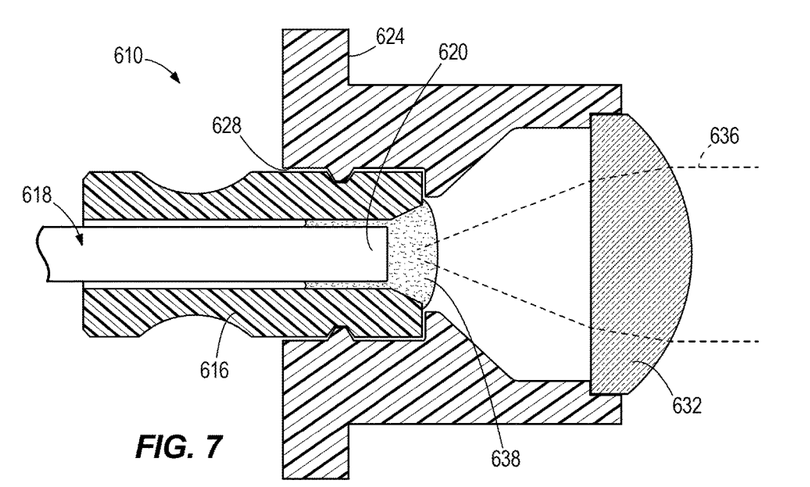
FIG. 7 illustrates a surgical instrument in accordance with another construction, having scattering material that directly contacts a proximal end of an optical fiber.

FIG. 7 illustrates a surgical instrument 610 according to another construction of the invention. The surgical instrument 610 includes a tube in the form of a connector 616 and a light source in the form of an optical fiber 618 extending through the connector 616. The optical fiber 618 has a proximal end 620 disposed within the connector 616. The surgical instrument 610 also includes a receptacle 624 coupled to the connector 616. The receptacle 624 is a housing that includes an opening 628 that receives at least a portion of the connector 616. In some constructions, the receptacle 624 is fixed during surgery, and/or is coupled to another component such as a light source housing. The surgical instrument 610 also includes a lens 632 coupled to the receptacle 624. As illustrated in FIG. 7, the lens 632 receives a light 636 (e.g., a monochromatic light source such as a green laser beam), and directs the light 636 toward the proximal end 620 of the optical fiber 618. Before the light 636 reaches the proximal end 620 of the optical fiber 618, the light 636 first passes through a scattering material 638 (e.g., the same type of material as the scattering material 238, 338, or 538). In the illustrated construction, the scattering material 638 directly contacts the proximal end 620 of the optical fiber 618, with at least a portion of the scattering material 638 being disposed between the proximal end 620 of the optical fiber 618 and the connector 616. In some constructions, the scattering material 638 is integrally formed in one piece with the proximal end 620 of the optical fiber 618. For example, in some constructions the proximal end 620 of the optical fiber 618 is heated, to melt some of the material (e.g., plastic) of the proximal end 620. The proximal end 620 is then pressed and twisted into a mold containing titanium and/or silicon dioxide powder. The powder is then embedded into the molten material and the proximal end 620 of the optical fiber 618 is shaped as desired. The scattering material 638 provides intense scattering, causing the light 636 to be mixed into a uniformly distributed output into the proximal end 620 of the optical fiber 618.

In the illustrated construction in FIG. 7, the light 636 is a monochromatic green laser light. In other constructions, the light 636 is a combination of separate red, green and blue lights, the separate lights being combined by the lens 632 into a polychromatic output which is perceived as white. While the illustrated light 636 comes from a laser light source, in other constructions a non-laser light source, such as a xenon arc lamp, is used.

In the case of ophthalmic surgery, it is desirable to omit blue light (or to arrange for blue light to be selectively turned on or off). Intense blue light causes photochemical damage to the retina (a phenomenon known as phototoxicity). Combining green and red light gives an illumination, perceived as yellow, which is much less damaging than white illumination.

An alternative approach for a safe yellow illumination is to use a single green light, as illustrated in FIG. 7, and to produce a red component by means of phosphors in the scattering material 638. Such phosphors absorb light at a shorter wavelength (such as green or blue) and re-emit light at a longer wavelength (such as red or orange). Alternatively, a white illumination can be produced using a blue light and phosphors for the green and red light.

In the illustrated construction of FIG. 7, the scattering material 638 includes phosphors that are mixed together with scattering particles (e.g., micron-sized crystals of titanium dioxide and/or silicon dioxide) into an optical epoxy mixture (e.g., a matrix). While still fluid, this mixture can be cast into a desired shape and allowed to cure. The scattering material 638 is disposed at the focal point of the lens 632, which concentrates the light 636 (e.g., the green laser light) to a small spot with very high intensity. The scattering material 638, in which the phosphor re-emission occurs, thus acts as an emitter. Because the scattering material 638 is in direct contact with the proximal end 620 end of the optical fiber 618, efficient coupling to the optical fiber 618 is assured.

Figure 8:
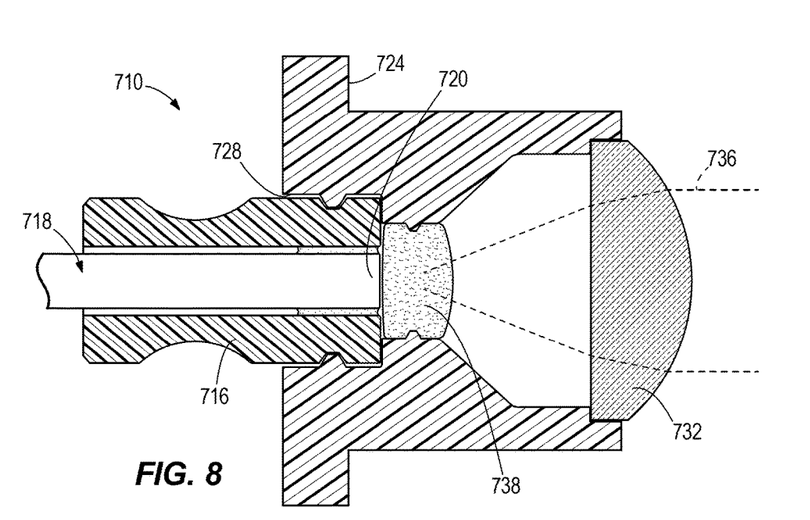
FIG. 8 illustrates a surgical instrument in accordance with another construction, having scattering material that directly contacts a receptacle and spaced from a proximal end of an optical fiber.

FIG. 8 illustrates a surgical instrument 710 according to another construction of the invention. The surgical instrument 710 includes a tube in the form of a connector 716 and a light source in the form of an optical fiber 718 extending through the connector 716. The optical fiber 718 has a proximal end 720 disposed within the connector 716. The surgical instrument 710 also includes a receptacle 724 coupled to the connector 716. The receptacle 724 is a housing that includes an opening 728 that receives at least a portion of the connector 716. In some constructions, the receptacle 724 is fixed during surgery, and/or is coupled to another component such as a light source housing. The surgical instrument 710 also includes a lens 732 coupled to the receptacle 724. As illustrated in FIG. 7, the lens 732 receives a light 736 (e.g., a monochromatic light such as a green laser beam), and directs the light 736 toward the proximal end 720 of the optical fiber 718. Before the light 736 reaches the proximal end 720 of the optical fiber 718, the light 736 first passes through a scattering material 738 (e.g., the same type of material as scattering material 238, 338, 538, or 638). In the illustrated construction, the scattering material 738 includes phosphors, directly contacts the receptacle 724, and is indirectly coupled to the proximal end 720 of the optical fiber 718 (illustrated by a gap in FIG. 8 between the scattering material 738 and the proximal end 720 of the optical fiber 718). This reduces the cost of the surgical instrument 710, and also eliminates any concern about disposal of materials containing phosphors. On the down side, however, directing light into the optical fiber 718 is not as efficient as in the surgical instrument 610 shown in FIG. 7, where the scattering material 638 is directly coupled to the proximal end 620 of the optical fiber 618. While the illustrated light 736 comes from a laser light source, in other constructions a non-laser light source, such as a xenon arc lamp, is used.

Figure 9:
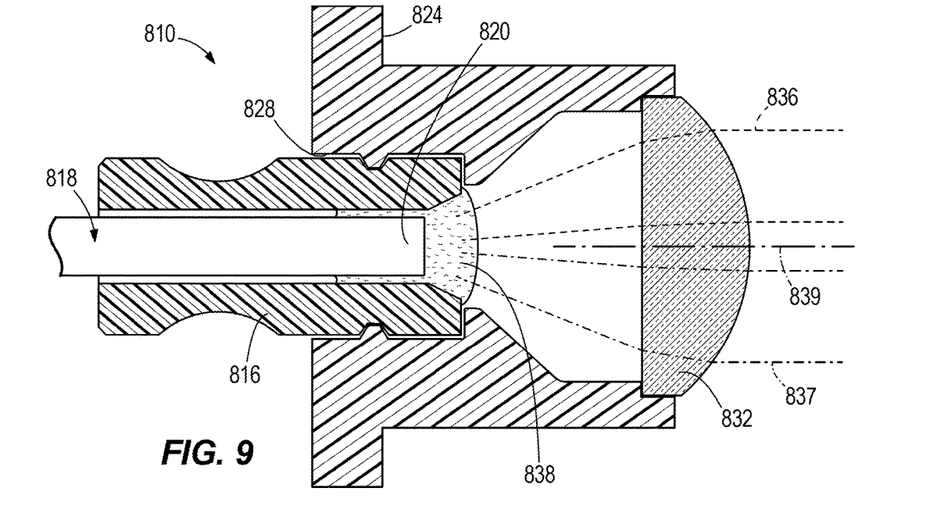
FIGS. 9 and 10 illustrate surgical instruments in accordance with other constructions, having multiple laser beams being directed to a proximal end of an optical fiber.

FIG. 9 illustrates a surgical instrument 810 according to another construction of the invention. The surgical instrument 810 includes a tube in the form of a connector 816 and a light source in the form of an optical fiber 818 extending through the connector 816. The optical fiber 818 has a proximal end 820 disposed within the connector 816. The surgical instrument 810 also includes a receptacle 824 coupled to the connector 816. The receptacle 824 is a housing that includes an opening 828 that receives at least a portion of the connector 816. In some constructions, the receptacle 824 is fixed during surgery, and/or is coupled to another component such as a light source housing. The surgical instrument 810 also includes a lens 832 coupled to the receptacle 824. As illustrated in FIG. 9, the lens 832 receives at least two types of light 836, 837 (e.g., a monochromatic green laser light and a monochromatic red laser light), and directs the two types of light 836, 837 toward the proximal end 820 of the optical fiber 818. Before the two types of light 836, 837 reach the proximal end 820 of the optical fiber 818, the two types of light 836, 837 first pass through a scattering material 838 (e.g., the same type of material as the scattering material 238, 338, 538, 638, or 738). In some constructions, the scattering material 838 is integrally formed in one piece with the proximal end 820 of the optical fiber 818, via a method similar to that described above for the scattering material 638. If the two types of light 836, 837 are both parallel to a central axis 839 of the lens 832, they will both be concentrated at a focal point of the lens 832. In the illustrated construction of FIG. 9, the scattering material 838, in the form of an epoxy mixture at the end of the connector 816, includes scattering particles (e.g., micron-sized crystals of titanium dioxide and/or silicon dioxide) but not phosphors. The scattering material 838 acts as a uniform emitter of polychromatic light, and is directly coupled to the proximal end 820 of the optical fiber 818. While the illustrated two types of lights 836, 837 come from laser light sources, in other constructions a non-laser light source or sources are used, such as a xenon arc lamp.

Figure 10:
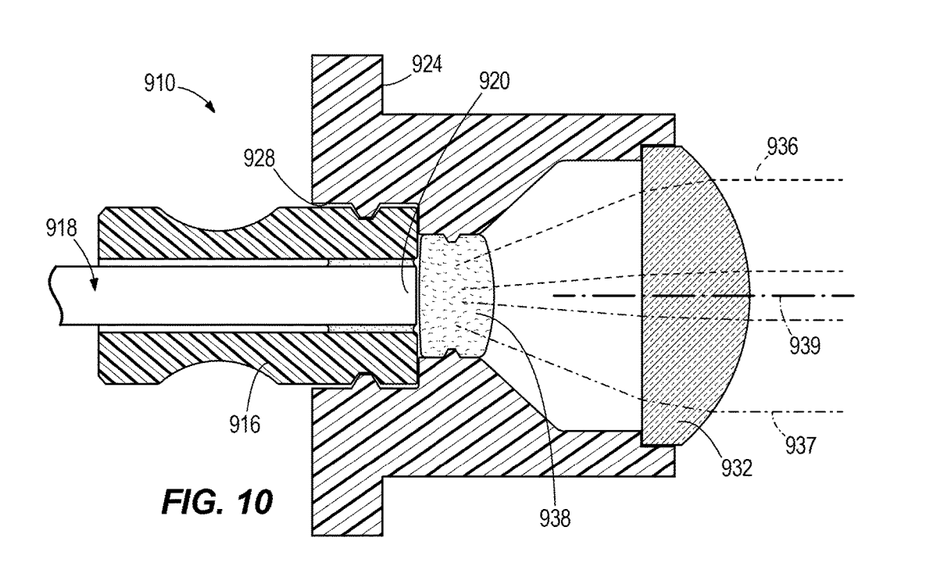

FIG. 10 illustrates a surgical instrument 910 according to another construction of the invention. The surgical instrument 910 includes a tube in the form of a connector 916 and a light source in the form of an optical fiber 918 extending through the connector 916. The optical fiber 918 has a proximal end 920 disposed within the connector 916. The surgical instrument 910 also includes a receptacle 924 coupled to the connector 916. The receptacle 924 is a housing that includes an opening 928 that receives at least a portion of the connector 916. In some constructions, the receptacle 924 is fixed during surgery, and/or is coupled to another component such as a light source housing. The surgical instrument 910 also includes a lens 932 coupled to the receptacle 924. As illustrated in FIG. 10, the lens 932 receives at least two types of light 936, 937 (e.g., a monochromatic green laser light and a monochromatic red laser light), and directs the two types of light 936, 937 toward the proximal end 920 of the optical fiber 918. Before the two types of light 936, 937 reach the proximal end 920 of the optical fiber 918, the two types of light 936, 937 first pass through a scattering material 938 (e.g., the same type of material as the scattering material 238, 338, 538, 638, 738, or 838). If the two types of light 936, 937 are both parallel to a central axis 939 of the lens 932, they will both be concentrated at a focal point of the lens 932. In the illustrated construction in FIG. 10, the scattering material 938 directly contacts the receptacle 924, and is indirectly coupled to the proximal end 920 of the optical fiber 918 (illustrated by a gap in FIG. 10 between the scattering material 938 and the proximal end 920 of the optical fiber 918). In the illustrated construction of FIG. 10 the scattering material 938, in the form of an epoxy mixture, includes scattering particles (e.g., micron-sized crystals of titanium dioxide and/or silicon dioxide) but not phosphors. The scattering material 838 acts as a uniform emitter of polychromatic light. While the illustrated two types of light 936, 937 come from laser light sources, in other constructions a non-laser light source or sources are used, such as a xenon arc lamp.

Figure 11:
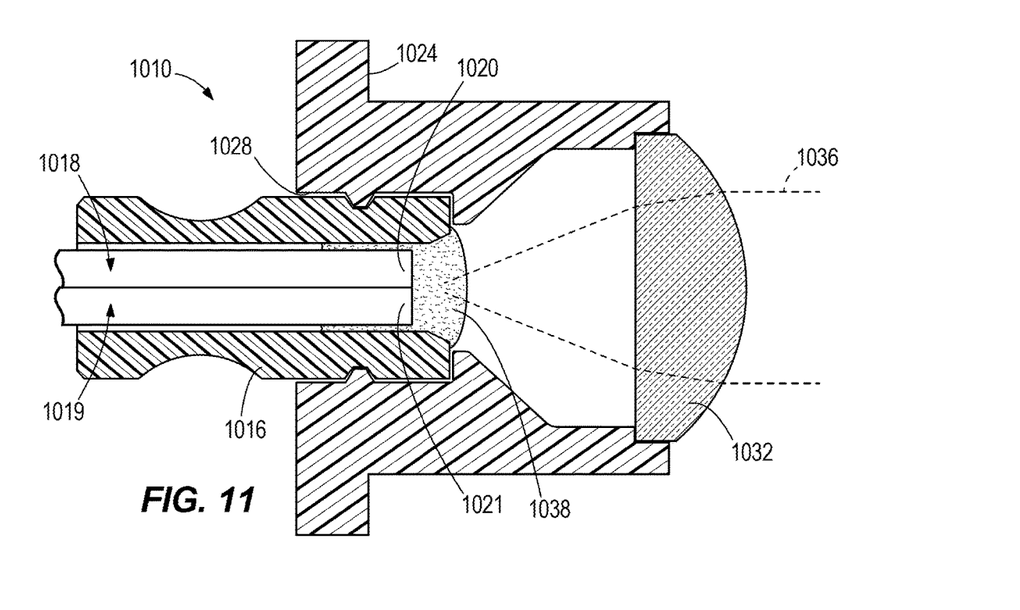
FIGS. 11 and 12 illustrate surgical instruments in accordance with other constructions, having two parallel optical fibers.

In some constructions, two or more optical fibers are used instead of the single optical fiber illustrated in FIGS. 1-10. For example, FIG. 11 illustrates a surgical instrument 1010 according to another construction of the invention. The surgical instrument 1010 includes a tube in the form of a connector 1016 and two light sources in the form of parallel optical fibers 1018, 1019 extending through the connector 1016. The optical fibers 1018, 1019 each have a proximal end 1020, 1021 disposed within the connector 1016. The surgical instrument 1010 also includes a receptacle 1024 coupled to the connector 1016. The receptacle 1024 is a housing that includes an opening 1028 that receives at least a portion of the connector 1016. In some constructions, the receptacle 1024 is fixed during surgery, and/or is coupled to another component such as a light source housing. The surgical instrument 1010 also includes a lens 1032 coupled to the receptacle 1024. As illustrated in FIG. 11, the lens 1032 receives light 1036 (e.g., a monochromatic light such as a green laser beam), and directs the light 1036 toward the proximal ends 1020, 1021 of the optical fibers 1018, 1019. Before the light 1036 reaches the proximal ends 1020, 1021 of the optical fibers 1018, 1019, the light 1036 first passes through a scattering material or materials 1038 (e.g., the same type of material as the scattering material 238, 338, 538, 638, 738, 838, 938). In the illustrated construction, the scattering material 1038 directly contacts the proximal ends 1020, 1021 of the optical fibers 1018, 1019, with at least a portion of the scattering material 1038 being disposed between the proximal ends 1020, 1021 of the optical fibers 1018, 1019 and the connector 1016. In some constructions, scattering materials 1038 are integrally formed in one piece with each of the proximal ends 1020, 1021 of the optical fibers 1018, 1019, via a method similar to that described above for the scattering material 638. The scattering material 1038 includes scattering particles (e.g., micron-sized crystals of titanium dioxide and/or silicon dioxide) and phosphors, and provides intense scattering, causing the light 636 to be mixed into a uniformly distributed output.

Figure 12:
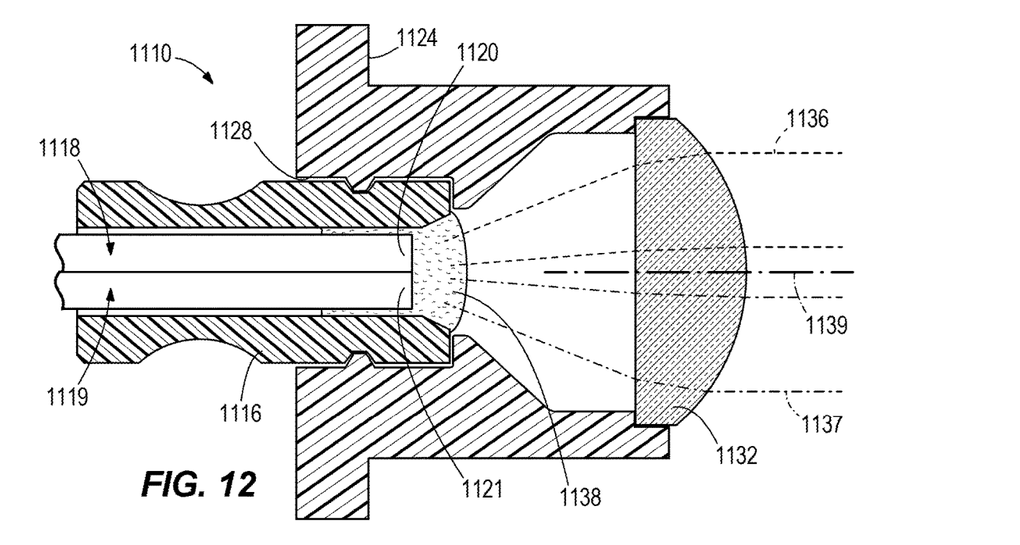

FIG. 12 illustrates a surgical instrument 1110 according to another construction of the invention. The surgical instrument 1110 includes a tube in the form of a connector 1116 and two light sources in the form of parallel optical fibers 1118, 1119 extending through the connector 1116. The optical fibers 1118, 1119 each have a proximal end 1120, 1121 disposed within the connector 1116. The surgical instrument 1110 also includes a receptacle 1124 coupled to the connector 1116. The receptacle 1124 is a housing that includes an opening 1128 that receives at least a portion of the connector 1116. In some constructions, the receptacle 1124 is fixed during surgery, and/or is coupled to another component such as a light source housing. The surgical instrument 1110 also includes a lens 1132 coupled to the receptacle 1124. As illustrated in FIG. 12, the lens 1132 receives at least two types of light 1136, 1137 (e.g., a monochromatic green laser light and a monochromatic red laser light), and directs the two types of light 1136, 1137 toward the proximal ends 1120, 1121 of the optical fibers 1118, 1119. Before the two types of light 1136, 1137 reach the proximal ends 1120, 1121 of the optical fibers 1118, 1119, the two types of light 1136, 1137 first pass through a scattering material or materials 1138 (e.g., the same type of material as the scattering material 238, 338, 538, 638, 738, 838, 938, 1038). In some constructions, the scattering materials 1138 are integrally formed in one piece with each of the proximal ends 1120, 1121 of the optical fibers 1118, 1119, via a method similar to that described above for the scattering material 638. If the two types of light 1136, 1137 are both parallel to a central axis 1139 of the lens 1132, they will both be concentrated at a focal point of the lens 1132. In the illustrated construction of FIG. 12 the scattering material 1138, in the form of an epoxy mixture at the end of the connector 1116, includes both scattering particles (e.g., micron-sized crystals of titanium dioxide and/or silicon dioxide) but not phosphors. The scattering material 1138 acts as a uniform emitter of polychromatic light, and is directly coupled to the proximal ends 1120, 1121 of the optical fiber 1118.

In some constructions, a first scattering material (e.g., one of the scattering materials 538, 738, 838, 938, 1038, or 1138) is coupled to a proximal end of a light source (e.g., the optical fiber 218, 318, 518, 718, 818, 918, 1018, 1019, 1118, or 1119), such that light entering the light source at the proximal end of the light source must first past through the first scattering material, and a second scattering material (e.g., one of the scattering materials 238, 338, or 538) is coupled to a distal end of the light source, such that light exiting the light source at the distal end of the light source must pass through the second scattering material. For example, in some constructions the features of the surgical instruments 710, 810, 910, 1010, or 1110 described above at the proximal end of an optical fiber are combined with the features of the surgical instruments 210, 310, or 510 described above at the distal end of the optical fiber. In one particular construction, for example, the two optical fibers 1018, 1019 of FIG. 11 each terminate at the distal ends of the optical fibers 1018, 1019 with the features of the chandelier-type surgical device 510 of FIG. 6. By placing the two chandelier-type surgical instruments 510 at different locations in the eye 34, shadows cast by the surgical instruments 510 are greatly reduced.

While the light sources (or more accurately, light carriers) described above are depicted as being in the form of optical fibers, other constructions include different types of light sources or carriers, including for example, light tubes and pipes. Additionally, while certain types of tubes are described above (e.g., needles, hubs, etc.) for housing and/or directing the light sources or carriers, in other constructions various other types of tubes may alternatively be used.

Although the invention has been described in detail with reference to certain preferred embodiments, variations and modifications exist within the scope and spirit of one or more independent aspects of the inventions as described.

What is claimed is:

1. A surgical instrument comprising:
    an optical fiber having a proximal end and a distal end, the optical fiber configured to move light along a pathway from the proximal end to the distal end and to emit the light at the distal end;
    a first scattering material coupled directly to the proximal end of the optical fiber, and
    a second scattering material that is coupled to the distal end of the optical fiber, wherein the first scattering material is positioned such that the light passes through the first scattering material prior to entering the proximal end of the optical fiber and moving along the pathway to the distal end.

2. The surgical instrument of claim 1, wherein the first scattering material is integrally formed in one piece with the proximal end of the optical fiber.

3. The surgical instrument of claim 1, further comprising a tube, wherein the optical fiber is disposed at least partially within the tube.

4. The surgical instrument of claim 3, wherein the tube is selected from one of a group consisting of a needle, a hub, and a connector.

5. The surgical instrument of claim 3, wherein the tube is a connector, wherein the surgical instrument further comprises a receptacle coupled to the connector and a lens coupled to the receptacle, wherein the proximal end of the optical fiber is disposed at least partially within the connector.

6. The surgical instrument of claim 5, wherein the lens is positioned to receive the light and to direct the light into the first scattering material.

7. The surgical instrument of claim 5, wherein the optical fiber is a first optical fiber, the surgical instrument further including a second optical fiber, each optical fiber having a proximal end disposed at least partially within the connector.

8. The surgical instrument of claim 1, wherein the first scattering material includes an epoxy mixture of both scattering particles and phosphors.

9. The surgical instrument of claim 1, wherein the first scattering material includes titanium dioxide.

10. The surgical instrument of claim 1, wherein the first scattering material includes silicon dioxide.

11. The surgical instrument of claim 1, wherein the second scattering material is directly coupled to the distal end of the optical fiber.

12. The surgical instrument of claim 1, wherein the optical fiber is plastic, and wherein the first scattering material includes powder embedded into the plastic.

13. The surgical instrument of claim 1, wherein the optical fiber is a first optical fiber, and wherein the surgical instrument further includes a second optical fiber that extends parallel to the first optical fiber.

14. The surgical instrument of claim 1, wherein the first scattering material at least partially surrounds the proximal end of the optical fiber.

15. A surgical instrument comprising:
    a receptacle;
    an optical fiber having a proximal end and a distal end, the proximal end coupled to the receptacle, the distal end disposed outside of the receptacle, the optical fiber configured to move light along a pathway from the proximal end to the distal end and to emit the light at the distal end;
    a scattering material disposed within the receptacle; and
    a lens coupled to the receptacle and spaced apart from the proximal end of the optical fiber and from the scattering material, wherein the lens is positioned to receive the light from a source outside of the receptacle and to pass the light through the lens and direct the light into the scattering material,
    wherein the scattering material is coupled directly to the proximal end of the optical fiber, wherein a first portion of the scattering material is disposed axially adjacent the proximal end of the optical fiber, and wherein a second portion of the scattering material extends circumferentially around the proximal end of the optical fiber.

\* \* \* \* \*